United States Patent [19]
Smith et al.

[11] Patent Number: 5,840,858
[45] Date of Patent: Nov. 24, 1998

[54] PROTEIN PURIFICATION USING IMMOBILIZED METAL AFFINITY CHROMATOGRAPHY FOR COMPLEMENT RECEPTOR PROTEINS

[75] Inventors: Thomas Michael Smith, Drexel Hill; Gail Folena-Wasserman, Richboro, both of Pa.

[73] Assignee: T Cell Sciences, Inc., Needham, Mass.

[21] Appl. No.: 581,604

[22] PCT Filed: Jul. 6, 1994

[86] PCT No.: PCT/US94/07555

§ 371 Date: Apr. 3, 1996

§ 102(e) Date: Apr. 3, 1996

[87] PCT Pub. No.: WO95/01797

PCT Pub. Date: Jan. 19, 1995

Related U.S. Application Data

[63] Continuation of Ser. No. 90,351, Jul. 9, 1993, abandoned.

[51] Int. Cl.$^6$ .................. C07K 1/22; C07K 1/36
[52] U.S. Cl. ................ 530/413; 530/380; 530/395
[58] Field of Search ................ 530/380, 395, 530/413

[56] References Cited

U.S. PATENT DOCUMENTS

| | | | |
|---|---|---|---|
| 5,169,936 | 12/1992 | Staples et al. | 530/350 |
| 5,252,216 | 10/1993 | Folena-Wasserman et al. | 210/635 |
| 5,256,642 | 10/1993 | Fearon et al. | 514/8 |

FOREIGN PATENT DOCUMENTS

| | | | |
|---|---|---|---|
| WO 90/07524 | 7/1990 | WIPO | C07K 15/00 |

OTHER PUBLICATIONS

Porath et al., Biochemistry, 22:1621–30 (1983).
Deutscher, Guide to Protein Purification (Academic Press, San Diego 1990), pp. 373–379.
Seya, et al., J. Immunology, 135(4):2261–7 (1985).
Sugita et al., J. Biochem., 100:1193–1200 (1986).
Suomela, Transfusion Medicine, 7(1):42–57 (Jan. 1993).
Kinoshita et al., J. Immunol., vol. 134(4), pp. 2564–2570, 1985.
Wong et al., J. Immunol., vol. 134(6), pp. 4048–4056, 1985.
Yoon et al., J. Immunol., vol. 134(5), pp. 3332–3338, 1985.
Seya et al. J. Immunol., vol. 135(4), pp. 2661–2667, 1985.
Sim, Biochem. J., vol. 232, pp. 883–889, 1985.
Nichello et al., Molecular Immunol., vol. 21(6), pp. 661–668, 1986.
Sigita et al., J. Biochem., vol. 100, pp. 1193–1200, 1986.
Wong et al., J. Immunol. Meth., 82:303–13 (1985).

Primary Examiner—Chhaya D. Sayala
Attorney, Agent, or Firm—Leon R. Yankwich

[57] ABSTRACT

This invention relates to the application of immobilized metal affinity chromatography to the purification of complement receptor proteins.

46 Claims, No Drawings

PROTEIN PURIFICATION USING IMMOBILIZED METAL AFFINITY CHROMATOGRAPHY FOR COMPLEMENT RECEPTOR PROTEINS

This application is a 371 of PCT94/07555 filed Jul. 6, 1994 which is a continuation of 08/09351 filed Jul. 9, 1993, now abandoned.

FIELD OF THE INVENTION

This invention relates to the field of protein purification. More specifically, this invention relates to the application of immobilized metal affinity chromatography to the purification of complement receptor proteins.

BACKGROUND OF THE INVENTION

Historically, protein purification schemes have been predicated on differences in the molecular properties of size, charge and solubility between the protein to be purified and undesired protein contaminants. Protocols based on these parameters include size exclusion chromatography, ion exchange chromatography, differential precipitation and the like.

Size exclusion chromatography, otherwise known as gel filtration or gel permeation chromatography, relies on the penetration of macromolecules in a mobile phase into the pores of stationary phase particles. Differential penetration is a function of the hydrodynamic volume of the particles. Accordingly, under ideal conditions the larger molecules are excluded from the interior of the particles while the smaller molecules are accessible to this volume and the order of elution can be predicted by the size of the protein because a linear relationship exists between elution volume and the log of the molecular weight. Size exclusion chromatographic supports based on cross-linked dextrans e.g. SEPHADEX®, spherical agarose beads e.g. SEPHAROSE® (both commercially available from Pharmacia AB. Uppsala, Sweden), based on cross-linked polyacrylamides e.g. BIO-GEL® (commercially available from BioRad Laboratories, Richmond, Calif.) or based on ethylene glycol-methacrylate copolymer e.g. TOYOPEARL HW65S (commercially available from ToyoSoda Co., Tokyo, Japan) are useful in the practice of this invention.

Precipitation methods are predicated on the fact that in crude mixtures of proteins the solubilities of individual proteins are likely to vary widely. Although the solubility of a protein in an aqueous medium depends on a variety of factors, for purposes of this discussion it can be said generally that a protein will be soluble if its interaction with the solvent is stronger than its interaction with protein molecules of the same or similar kind. Without wishing to be bound by any particular mechanistic theory describing precipitation phenomena, it is nonetheless believed that the interaction between a protein and water molecules occurs by hydrogen bonding with several types of uncharged groups, and electrostatically as dipoles with charged groups, and that precipitants such as salts of monovalent cations (e.g., ammonium sulfate) compete with proteins for water molecules, thus at high salt concentrations, the proteins become "dehydrated" reducing their interaction with the aqueous environment and increasing the aggregation with like or similar proteins resulting in precipitation from the medium.

Ion exchange chromatography involves the interaction of charged functional groups in the sample with ionic functional groups of opposite charge on an adsorbent surface. Two general types of interaction are known. Anionic exchange chromatography mediated by negatively charged amino acid side chains (e.g. aspartic acid and glutamic acid) interacting with positively charged surfaces and cationic exchange chromatography mediated by positively charged amino acid residues (e.g. lysine and arginine) interacting with negatively charged surfaces.

More recently affinity chromatography and hydrophobic interaction chromatography techniques have been developed to supplement the more traditional size exclusion and ion exchange chromatographic protocols. Affinity chromatography relies on the interaction of the protein with an immobilized ligand. The ligand can be specific for the particular protein of interest in which case the ligand is a substrate, substrate analog, inhibitor or antibody. Alternatively, the ligand may be able to react with a number of proteins. Such general ligands as adenosine monophosphate, adenosine diphosphate, nicotine adenine dinucleotide or certain dyes may be employed to recover a particular class of proteins. One of the least biospecific of the affinity chromatographic approaches is immobilized metal affinity chromatography (IMAC), also referred to as metal chelate chromatography. IMAC introduced by Porath et al.(*Nature* 258:598–99(1975) involves chelating a metal to a solid support and then forming a complex with electron donor amino acid residues on the surface of a protein to be separated.

Hydrophobic interaction chromatography was first developed following the observation that proteins could be retained on affinity gels which comprised hydrocarbon spacer arms but lacked the affinity ligand. Although in this field the term hydrophobic chromatography is sometimes used, the term hydrophobic interaction chromatography (HIC) is preferred because it is the interaction between the solute and the gel that is hydrophobic not the chromatographic procedure. Hydrophobic interactions are strongest at high ionic strength, therefore, this form of separation is conveniently performed following salt precipitations or ion exchange procedures. Elution from HIC supports can be effected by alterations in solvent, pH, ionic strength, or by the addition of chaotropic agents or organic modifiers, such as ethylene glycol. A description of the general principles of hydrophobic interaction chromatography can be found in U.S. Pat. No. 3,917,527 and in U.S. Pat. No. 4,000,098. The application of HIC to the purification of specific proteins is exemplified by reference to the following disclosures: human growth hormone (U.S. Pat. No. 4,332,717), toxin conjugates (U.S. Pat. No. 4,771,128), antihemolytic factor (U.S. Pat. No. 4,743,680), tumor necrosis factor (U.S. Pat. No. 4,894,439), interleukin-2 (U.S. Pat. No. 4,908,434), human lymphotoxin (U.S. Pat. No. 4,920,196) and lysozyme species (Fausnaugh, J. L. and F. E. Regnier, *J. Chromatog.* 359:131–146 (1986)).

This invention relates to the application of a combination of ion exchange, IMAC, HIC and size exclusion chromatography to the purification of complement receptor molecules and complement receptor-like molecules.

BRIEF DESCRIPTION OF THE INVENTION

This invention relates to a method for purifying a complement receptor protein from a mixture containing same comprising sequentially contacting said mixture with a cationic chromatographic support, metal affinity chromatographic support, a size exclusion chromatographic support and selectively eluting the protein from each support.

In another aspect the invention provides for the purification of a complement receptor protein from conditioned cell culture medium containing same comprising sequentially subjecting the medium to (a) a first cationic exchange chromatography, (b) immobilized metal affinity chromatography, (c) hydrophobic interaction chromatography, (d) anionic exchange chromatography, and (e) size exclusion chromatography.

In another aspect this invention provides a method for purifying a complement receptor protein from a conditioned cell medium comprising:

(a) concentrating the conditioned cell medium;

(b) adsorbing the complement receptor protein onto a cationic chromatographic support;

(c) washing the adsorbed protein with at least one buffer;

(d) eluting the washed protein onto an imnnobilized metal affinity chromatographic support;

(e) adsorbing the eluted protein from step (d);

(f) washing the adsorbed protein with at least one buffer;

(g) eluting the washed protein;

(h) adsorbing the eluted protein from step (g) onto a hyrophobic interaction chromatographic support;

(i) selectively eluting the protein;

(j) adsorbing the eluate from step (i) onto an anionic exchange support;

(k) eluting the adsorbed protein;

(l) subjecting the eluate from step (k) to size exclusion chromatography and (m) recovering the protein therefrom.

DETAILED DESCRIPTION OF THE INVENTION

This invention relates to protein purification techniques which have application to the large scale purification of complement receptor proteins. The invention is particularly useful because it permits the recovery of receptor protein of >95% protein purity. The invention may be applied to the purification of a number of complement receptor proteins and complement receptor-like proteins.

Complement is a group of serum proteins, sequentially activated by limited proteolysis, that are important effectors of humoral immunity. Activation of complement occurs by interaction of early acting complement components with antigen/antibody complexes. Proteolytic fragments resulting from this activation alone or with other proteins activate additional complement proteins resulting in a proteolytic cascade reminiscent of the functioning of blood clotting factors. Alternatively, complement can be activated by bacterial cell wall components, proteolytic enzymes (e.g. plasmin) or complex carbohydrates (e.g. inulin). A number of biological activities are mediated by components of the complement system (e.g. immune cytolysis, anaphylatoxin production, bacteriolysis, chemotaxsis, hemolysis, opsonization, and phagocytosis).

Four classes of complement receptors (CR) are known (CR1–CR4). Complement receptor 1 (CR1) is a receptor for complement components C3b and C4b. Complement receptor 2 (CR2) is a receptor for component C3dg or C3d. Complement receptor 3 (CR3) is a receptor for C3bi. Complement receptor 4 (CR4) is a receptor for C3dg.

Complement receptor type 1 (CR1) is present on the membranes of erythrocytes, monocytes/macrophages, granulocytes, B cells, some T cells, splenic follicular dendritic cells, and glomerular podocytes. CR1 binds C3b and C4b and is referred to as the C3b/C4b receptor. Its primary sequence has been determined (Klickstein et al., *J. Exp. Med.* 165: 1095–1112 (1987), Klickstein et al., *J. Exp. Med.* 168:1699–(1988); Hourcade et al., *J. Exp Med.* 168:1255–1270 (1988)). It is composed of 30 short consensus repeats (SCRs) that contain 60–70 amino acids, of which 29 of the average 65 amino acids per SCR are conserved. It is proposed that each SCR forms a three dimensional triple loop structure tough disulfide linkages with the third and first and the fourth and second half-cystines in disulfide bonds. The SCRs are further organized into 4 long homologous repeats (LHRs) of 7 SCRs each. Following a leader sequence, the molecule consists of the most N-terminal LHR-A comprising a C4b binding domain, the next two repeats, LHR-B and LHR-C comprising C3b binding domains, and the most C terminal LHR-D followed by 2 additional SCRs, a 25 residue putative transmembrane region and a 43 residue cytoplasmic tail.

CR1 is a member of a superfamily characterized by SCR homology. This superfamily contains members that also have a C3/C4 binding function, such as CR2, C4bp, factor H, factor B, and C2, as well as proteins without this function, such as interleukin-2 receptor, b2-glycoprotein I, C1r, haptoglobin a chain, and factor XIIIb.

CR1 is known to be a glycoprotein and its deduced amino acid sequence has 24 potential sites for N-linked oligosaccharides in the extracellular region. However, the synthesis of CR1 in the presence of tunicamycin (Lublin et al., *J. Biol. Chem.* 261: 5736 (1986)) and analysis of glucosamine content (Sim, *Biochem J.* 232: 883 (1985)) has suggested that only 6–8 of the available sites are actually linked to oligosaccharides. The N-terminus of the glycoprotein appears to be blocked.

Four different CR1 allotypes exist that differ in size by 30–50 kD increments. The gene frequencies of these allelic polymorphisms (allotypes) differ in the human population (Holer et al., *Proc. Natl. Acad. Sci.* U.S.A. 84:2459–2463 (1987)). The F (or A) allotype is composed of 4 LHRs and is about 250 kD; the larger S (or B) allotype contains a fifth LHR that is a chimera of the 5' half of LHR-B and the 3' half of LHR-A and is predicted to have a third C3b binding site (Wong et al., *J. Exp. Med.* 169: 847 (1989)), and is about 290 kD. The smallest F' (or C) allotype has increased incidence in patients with systemic lupus erythematosis (SLE) (Van Dyne et al., *Clin. Exp. Immunol.* 68:570 (1987) and Dykman et al., *Proc. Natl. Acad Sci. USA* 80: 1698 (1983)) and most likely arises from the deletion of LHR-B and one C3b binding site.

A naturally occurring soluble form of CR1 has been detected in the plasma of normal individuals and certain individuals with SLE (Yoon & Fearon *J. Immunol.* 134: 3332–3338 (1985)). Its characteristics are similar to those of erythocyte (cell-surface) CR1 both structurally and functionally.

Hourcade et al. (*J. Exp. Med.* 168: 1255–1270 (1998)) also observed an alternative polyadenylation site in the human CR1 transcriptional unit that was predicted to produce a secreted form of CR1. The mRNA that arises from this truncated sequence comprises the first 8.5 SCRs of CR1; e.g., the C4b binding domain, and could encode a protein of about 80 kD. When a cDNA corresponding to this truncated sequence was transfected into COS cells and expressed, it demonstrated the expected C4b, but not C3b binding activity (Kyrch et al., *F.A.S.E.B J.* 3:A368 (1989)). Krych et al. also observed a mRNA similar to the predicted one in several human cell lines and postulated that such a truncated soluble form of CR1 that is able to bind C4b may be synthesized in man.

Several soluble fragments of CR1 have also been generated via recombinant DNA procedures by eliminating the transmembrane region from the DNAs being expressed (Fearon et al., Intl. Patent Publication Number WO89/09220, published Oct. 5, 1989 and Fearon et al. Intl. Patent Publication WO091/05047 published Apr. 18, 1991). The soluble CR1 fragments were functionally active, since they were able to bind C3b and/or C4b and demonstrate factor I cofactor activity depending upon the regions they contained. In addition they were able to act as inhibitors of in vitro CR1 functions such as neutrophil oxidative burst, complement mediated hemolysis, and C3a and C5a production. A soluble CR1 construct, encoded by plasmid sCR1/pBSCR1c, also demonstrated in vivo activity in a reversed passive arthus reaction (Fearon et al. 1989 & 1991 and Yeh et al., J. Immunol (1991)) and suppressed post-ischemic myocardial inflammation and necrosis (Fearon et al. 1989 & 1990 and Weisman et al., Science 249: 146–151 (1990)). Furthermore, co-formulation of the sCR1/pBSCR1c product with p-anisoylated human plasminogen-streptokinase-activator complex (APSAC resulted in similar antihemolytic activity as APSAC alone, indicating that the combination of the complement inhibitor, sCR1, with a thrombolytic agent, could be a useful combination therapy (Fearon et al., Intl. Patent Publication Number WO091/05047 published Apr. 18, 1991).

Complement receptor-like proteins are proteins which may be purified by the protocol described herein, such protocol being modified if necessary by routine, non-inventive adjustments that do not entail undue experimentation. Such proteins include allotypes and alleles of CRs, truncated forms, chemically modified forms such as by PEG treatment, and fusion proteins containing a CR moiety. These proteins are referred to as complement receptor-like because they possess or retain sufficient CR protein properties to admit to purification by the process of this invention. Unless specifically identified otherwise, term complement receptor protein also includes complement receptor-like proteins. CR-1-like proteins represent a subset of CR-like proteins including alleles, truncates, chemically modified and fusion proteins derived from the CR-1 allotype. Soluble complement receptor 1 (sCR1), defined herein as a soluble form of human CR1 containing all 30 extracellular SCR domains, is a specific example of a CR-1-like protein.

The complement receptor proteins of this invention can be made by a variety of techniques. If full length native chains are required, then the native molecules may be extracted from the above-identified cell sources. When soluble forms are desired, fragments of the native full length molecules are preferred. Accordingly, DNAs encoding the desired chain fragments, are expressed as recombinantly produced protein fragments. This invention is particularly useful for the purification of sCR1 from conditioned cell culture medium of a variety of sCR1 producing recombinant cell lines. Although one may expect some variation from cell line to cell line and among the various complement receptor products, based on the disclosure herein, it is well within the purview of one of ordinary skill in this art to adapt the invention herein to a particular combination of complement receptor protein and producing cell line.

Generally, genes encoding proteins such as complement receptors may be cloned by incorporating DNA fragments coding for the desired regions of the polypeptide into a recombinant DNA vehicle (e.g., vector) and transforming or tansfecting suitable prokaryotic or eukaryotic hosts. Suitable prokaryotic hosts include but are not limited to Escherichia, Streptomyces, Bacillus and the like. Suitable eukaryotic hosts include but are not limited to yeast, such as Saccharomyces and animal cells in culture such as VERO, HeLa, mouse C127, Chinese hamster ovary (CHO), WI-38, BHK, COS, MDCK, and insect cell lines. Particularly preferred host are CHO cell lines deficient in dihydrofolate reductase such as ATCC CRL 1793, CRL 9096 and other cell lines described hereinbelow. Such recombinant techniques have now become well known and are described in Methods in Enzymology, (Academic Press) Volumes 65 and 69 (1979), 100 and 101 (1983), and the references cited therein. An extensive technical discussion embodying most commonly used recombinant DNA methodologies can be found in Maniatis, et al., Molecular Cloning, Cold Spring Harbor Laboratory (1982) or Current Protocols in Molecular Biology, Greene Publishing (1988,1991).

One way of obtaining a DNA fragment encoding a desired polypeptide such as a complement receptor is via cDNA cloning. In this process, messenger RNA (mRNA) is isolated from cells known or suspected of producing the desired protein. Through a series of enzymatic reactions, the mRNA population of the cells is copied into a complementary DNA (cDNA). The resulting cDNA is then inserted into cloning vehicles and subsequently used to transform a suitable prokaryotic or eukaryotic host. The resulting cDNA "library" is comprised of a population of transformed host cells, each of which contain a single gene or gene fragment. The entire library, in theory, provides a representative sample of the coding information present in the mRNA mixture used as the starting material.

The libraries can be screened using nucleic acid or antibody probes in order to identify specific DNA sequences. Once isolated, these DNA sequences can be modified or can be assembled into complete genes. Alternatively, as described in this invention, specific fragments of a gene can be engineered independently of the rest of the gene. Protein fragments encoded by these engineered gene fragments may not be found in nature, yet they may have significant utility in the treatment of undesirable physiological conditions. The genetic engineering of soluble complement receptor for the prevention and/or treatment of disorders involving complement activity is one such case.

Once the gene or gene fragment has been cloned, the DNA may introduced into an expression vector and that construction used to transform an appropriate host cell. An expression vector is characterized as having expression control sequences as defined herein, such that when a DNA sequence of interest is operably linked thereto, the vector is capable of directing the production of the product encoded by the DNA sequence of interest in a host cell containing the vector. With specific reference to this invention, it is possible to assemble fragments of a single coding sequence such that upon expression a soluble receptor protein is formed. A particularly efficacious application of this protocol to SCR1 recombinant production is found in the Fearon, et al. PCT Applications WO89/09220, published Oct. 5, 1989, and WO91/05047 published on Apr. 18, 1991, cited above.

After the recombinant product is produced it is desirable to recover the product. If the product is exported by the cell producing it, the product can be recovered directly from the cell culture medium. If the product is retained intracellularly, the cells must be physically disrupted by mechanical, chemical or biological means in order to obtain the intracellular product.

In the case of a protein product, the purification protocol should not only provide a protein product that is essentially free of other proteins, by which is meant at least 80% and preferably greater than 95% pure with respect to total protein in the preparation, but also eliminate or reduce to acceptable levels other host cell contaminants, DNA, RNA, potential pyrogens and the like.

As mentioned above, a variety of host cells may be used for the production of the receptors of this invention. The choice of a particular host cell is well within the purview of the ordinary skilled artisan taking into account, inter alia, the nature of the receptor, its rate of synthesis, its rate of decay and the characteristics of the recombinant vector directing the expression of the receptor. The choice of the host cell expression system dictates to a large extent the nature of the cell culture procedures to be employed. The selection of a particular mode of production be it batch or continuous, spinner or air lift, liquid or immobilized can be made once the expression system has been selected. Accordingly, fluidized bed bioreactors, hollow fiber bioreactors, roller bottle cultures, or stirred tank bioreactors, with or without cell microcarrier may variously be employed. The criteria for such selection are appreciated in the cell culture art. They are not detailed herein because they are outside the scope of this invention. This invention relates to the purification of complement receptors given their existence in a conditioned cell culture medium.

As mentioned above this invention relates, inter alia, to application of immobilized metal affinity chromatography (IMAC) to the purification of complement receptor proteins. The principles of IMAC are generally appreciated. It is believed that adsorption is predicated on the formation of a metal coordination complex between a metal ion, immobilized by chelation on the adsorbent matrix, and accessible electron donor amino acids on the surface of the protein to be bound. The metal-ion microenvironment including, but not limited to, the matrix, the spacer arm, if any, the chelating ligand, the metal ion, the properties of the surrounding liquid medium and the dissolved solute species can be manipulated by the skilled artisan to affect the desired fractionation.

Not wishing to be bound by any particular theory as to mechanism, it is further believed that the more important amino acid residues in terms of binding are histidine, tryptophan and probably cysteine. Since one or more of these residues are generally found in proteins, one might expect all proteins to bind to IMAC columns. However, the residues not only need to be present but also accessible (e.g., oriented on the surface of the protein) for effective binding to occur. To that end this invention also contemplates the addition of appropriate residues to the complement receptor proteins of interest. The residues, for example poly-histidine tails added to the amino terminus or carboxy terminus of the protein, can be engineered into the recombinant expression systems described herein by following the protocols described in U.S. Pat. No. 4,569,794.

The nature of the metal and the way it is coordinated on the column can also influence the strength and selectivity of the binding reaction. Matricies of silica gel, agarose and synthetic organic molecules such as polyvinyl-methacrylate co-polymers can be employed. The matricies preferably contain substituents to promote chelation. Substituents such as iminodiacetic acid (IDA) or its tris (carboxymethyl) ethylene diamine (TED) can be used. IDA is preferred. A particularly useful IMAC material is a polyvinyl methacrylate co-polymer substituted with IDA available commercially, e.g., as TOYOPEARL AF-CHELATE 650M (ToyoSoda Co.; Tokyo. The metals are preferrably divalent members of the first transition series through to zinc. Although $Co^{++}$, $Ni^{++}$, $Cd^{++}$ and $Fe^{+++}$ can be used. An important selection parameter is, of course, the affinity of the protein to be purified for the metal. $Cu^{++}$ is preferred. Of the four coordination positions around these metal ions, at least one is occupied by a water molecule which is readily replaced by a stronger electron donor such as a histidine residue at slightly alkaline pH.

In practice the IMAC column is "charged" with metal by pulsing with a concentrated metal salt solution followed by water or buffer. The column often acquires the color of the metal ion (except for zinc). Often the amount of metal is chosen so that approximately half of the column is charged. This allows for slow leakage of the metal ion into the non-charged area without appearing in the eluate. A pre-wash with intended elution buffers is usually carried out. Sample buffers may contain salt up to 1M or greater to minimize nonspecific ion-exchange effects. Adsorption of proteins is maximal at higher pHs. Elution is normally either by lowering of pH to protonate the donor groups on the adsorbed protein, or by the use of stronger complexing agent such as imidazole, or glycine buffers at pH 9. In these latter cases the metal may also be displaced from the column. Linear gradient elution procedures can also be benefically employed.

As mentioned above IMAC is particularly useful when used in combination with other protein purification techniques. That is to say it is preferred to apply IMAC to material that has been partially purified by other protein purification procedures. By the term "partially purified" is meant a protein preparation in which the protein of interest is present in at least 5 percent by weight, more preferably at least 10% and most preferably at least 45%. Accordingly, the application of IMAC is best appreciated in the context of an overall purification protocol for complement receptor proteins. A particularly useful combination chromatographic protocol is disclosed in U.S. Pat. No. 5,252,216 granted 12 Oct. 1993, the contents of which are incorporated herein by reference. It has been found to be useful, for example, to subject a sample of conditioned cell culture medium to partial purification prior to the application of IMAC. By the term "conditioned cell culture medium" is meant a cell culture medium which has supported cell growth and/or cell maintenance and contains secreted product. A concentrated sample of such medium is subjected to one or more protein purification steps prior to the application of a IMAC step. The sample may be subjected to ion exchange chromatography as a first step. As mentioned above various anionic or cationic substituents may be attached to matrices in order to form anionic or cationic supports for chromatography. Anionic exchange substituents include diethylaminoethyl (DEAE), quaternary aminoethyl(QAE) and quaternary amine(Q) groups. Cationic exchange substituents include carboxymethyl (CM), sulfoethyl(SE), sulfopropyl(SP), phosphate(P) and sulfonate(S). Cellulosic ion exchange resins such as DE23, DE32, DE52, CM-23, CM-32 and CM-52 are available from Whatman Ltd. Maidstone, Kent, U.K. SEPHADEX®-based and cross-linked ion exchangers are also known. For example, DEAE-, QAE-, CM-, and SP-dextran supports under the tradename SEPHADEX® and DEAE-, Q-, CM-and S-agarose supports under the tradename SEPHAROSE® are all available from Pharmacia AB. Further both DEAE and CM derivitized ethylene glycol-methacrylate copolymer such as TOYOPEARL DEAE-650S and TOYOPEARL CM-650S are available from Toso Haas Co., Philadelphia, Pa. Because elution from ionic supports usually involves addition of salt and because, as mentioned previously IMAC is enhanced under increased salt concentrations, the introduction of a IMAC step following an ionic exchange chromatographic step or other salt mediated purification step is particularly preferred. Additional purification protocols may be added including but not necessarily limited to HIC, further ionic exchange chromatography, size exclusion chromatography, viral inactivation, concentration and freeze drying.

Hydrophobic molecules in an aqueous solvent will self-associate. This association is due to hydrophobic interactions. It is now appreciated that macromolecules such as proteins have on their surface extensive hydrophobic patches in addition to the expected hydrophilic groups. HIC is predicated, in part, on the interaction of these patches with hydrophobic ligands attached to chromatographic supports. A hydrophobic ligand coupled to a matrix is variously referred to herein as an HIC support, HIC gel or HIC column. It is further appreciated that the strength of the interaction between the protein and the HIC support is not only a function of the proportion of non-polar to polar surfaces on the protein but by the distribution of the non-polar surfaces as well.

A number of matrices may be employed in the preparation of HIC columns, the most extensively used is agarose. Silica and organic polymer resins may be used. Useful hydrophobic ligands include but are not limited to alkyl groups having from about 2 to about 10 carbon atoms, such as a butyl, propyl, or octyl; or aryl groups such as phenyl. Conventional HIC products for gels and columns may be obtained commercially from suppliers such as Pharmacia LKB AB, Uppsala, Sweden under the product names butyl-SEPHAROSE®, phenyl-SEPHAROSE® CL-4B, octyl-SEPHAROSE® FF and phenyl-SEPHAROSE® FF; Tosoh Corporation, Tokyo, Japan under the product names TOYO-PEARL Butyl 650, Ether-650, or Phenyl-650 (FRACTOGEL TSK Butyl-650) or TSK-GEL phenyl-5PW; Miles-Yeda, Rehovot, Israel under the product name ALKYL-AGAROSE, wherein the alkyl group contains from 2–10 carbon atoms, and J. T. Baker, Phillipsburg, N.J. under the product name BAKERBOND WP-HI-propyl.

Ligand density is an important parameter in that it influences not only the strength of the interaction but the capacity of the column as well. The ligand density of the commercially available phenyl or octyl phenyl gels is on the order of 40 μmoles/ml gel bed. Gel capacity is a function of the particular protein in question as well pH, temperature and salt concentration but generally can be expected to fall in the range of 3–20 mg/ml of gel.

The choice of a particular gel can be determined by the skilled artisan. In general the strength of the interaction of the protein and the HIC ligand increases with the chain length of the of the alkyl ligands but ligands having from about 4 to about 8 carbon atoms are suitable for most separations. A phenyl group has about the same hydrophobicity as a pentyl group, although the selectivity can be quite different owing to the possibility of pi-pi interaction with aromatic groups on the protein.

Adsorption of the proteins to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}<Ca^{++}<Mg^{++}<Li^+<Cs^+<Na^+<K^+<Rb^+<NH_4^+$. While anions may be ranked in terms of increasing chaotropic effect as $PO_4^{---}<SO_4^{--}<CH_3COO^-<Cl^-<Br^-<NO_3^-<ClO_4^-<I^-<SCN^-$.

Accordingly, salts may be formulated that influence the strength of the interaction as given by the following relationship:

$$Na_2SO_4>NaCl>(NH_4)_2SO_4>NH_4Cl>NaBr>NASCN$$

In general, salt concentrations of between about 0.75 and about 2M ammonium sulfate or between about 1 and 4M NaCl are useful.

The influence of temperature on HIC separations is not simple, although generally a decrease in temperature decreases the interaction. However, any benefit that would accrue by increasing the temperature must also be weighed against adverse effects such an increase may have on the activity of the protein.

Elution, whether stepwise or in the form of a gradient, can be accomplished in a variety of ways: (a) by changing the salt concentration, (b) by changing the polarity of the solvent or (c) by adding detergents. By decreasing salt concentration adsorbed proteins are eluted in order of increasing hydrophobicity. Changes in polarity may be affected by additions of solvents such as ethylene glycol or (iso)propanol thereby decreasing the strength of the hydrophobic interactions. Detergents function as displacers of proteins and have been used primarily in connection with the purification of membrane proteins.

When the eluate resulting from HIC is subjected to further ion exchange chromatography, both anionic and cationic procedures may be employed.

As mentioned above, gel filtration chromatography affects separation based on the size of molecules. It is in effect a form of molecular sieving. It is desirable that no interaction between the matrix and solute occur, therefore, totally inert matrix materials are preferred. It is also desirable that the matrix be rigid and highly porous. For large scale processes rigidity is most important as that parameter establishes the overall flow rate. Traditional materials such as crosslinked dextran or polyacrylamide matrices, commercially available as, e.g., SEPHADEX® and BIOGEL®, respectively, were sufficiently inert and available in a range of pore sizes, however these gels were relatively soft and not particularly well suited for large scale purification. More recently, gels of increased rigidity have been developed (e.g. SEPHACRYL®, ULTROGEL®, FRACTOGEL® and SUPEROSE®). All of these materials are available in particle sizes which are smaller than those available in traditional supports so that resolution is retained even at higher flow rates. Ethylene glycol-methacrylate copolymer matrices, e.g., such as the TOYOPEARL HW series matrices (Toso Haas) are preferred.

For purposes of illustration only, this invention was applied to the purification of a complement receptor of the soluble type. More specifically, to a soluble CR1 construct containing leader, LHR-A, LHR-B, LHR-C, LHR-D, SCR29, SCR30 regions up to and including the first alanine residue of the transmembrane region; and corresponding to the CR1 encoding sequences in plasmid pBSCR1c of Fearon et al.; 1989, Int'l. Patent Publication Number WO89/09220, published Oct. 5, 1989 (hereinafter "TP10HD"). The construction of a recombinant system for the production of TP10HD is detailed in the above mentioned PCT Application and summarized as follows.

CHO cells were trypsinized and plated out at $5\times10^5$ per 60 mm dish and left in the growth medium (Hams F12 nutrient medium (041-1765) with 1% stock glutamine (043-05030), 1% stock pen/strep (043-05070) and 10% bovine fetal calf serum (011-6290),Gibco, Paisley, Scotland) at 37° C. in a humidified incubator in an atmosphere of 5% $CO_2$/95% air.

After 21 hours the cells were used for DNA transfection. An expression plasmid containing the sCR1 coding sequence from pBSCR1c was co-transfected with pSV2dhfr into a dhfr-requiring Chinese Hamster Ovary cell line (CHODUXBII). The transfection was carried in growth medium and employed the calcium coprecipitation/ glycerol shock procedure as described in:DNA Cloning, D. M. Glover ed. (Chap. 15, C. Gorman). Following transfection with pBSCR1c/pTCSgpt and pSV2dhfr, the cells were maintained in growth medium for 46 hours under growth conditions (as described above) prior to the selection procedure.

The selection and co-amplification procedure was carried out essentially as described by R. J. Kaufman, et al.(*Mol. Cell. Biol.* 5:1750–1759 (1985)). Forty-six hours post transfection the cells were changed to selective medium MEM ALPHA (041-02571), 1% stock glutamine, 1% stock pen/strep (043-05070) and dialysed bovine fetal calf serum (220-6300AJ) (Gibco, Paisley, Scotland). The cells were maintained in the selective medium for 8–10 days until dhfr$^+$ colonies appeared. When the colonies were established the cells were changed into a selective medium containing methotrexate, (A6770, Sigma Chem. Co., St. Louis, Mo.). The methotrexate concentration was initially 0.02 $\mu$M and was increased stepwise to 5 $\mu$M. During the amplification procedure aliquots of growth medium from growing cells were assayed for TP10HD production by ELISA. Any complement receptor secreting recombinant cell line (e.g. ATCC CRL 10052) may be used to supply the conditioned medium for purification according to this invention, but a particular cell line certainly is not required.

A transfected CHO cell line capable of producing TP10HD can be cultured by a variety of cell culture techniques. For the application of this invention the particular method of culturing is not critical, however for purposes of illustration, one method for cell culturing which may be used is a continuous perfusion process predicated on the VERAX fluidized bed technology as embodied in U.S. Pat. Nos. 4,861,714; 4,863,856; 4,978,616 and 4,997,753, the contents of which are incorporated by reference. Accordingly, transfected cells such as those described above, are scaled up in CCM-3 medium (a mixture of DMEM, Ham's F-12, bovine serum albumin and other nutrient supplements) supplemented with 10% fetal bovine serum (PBS) and 5 mM methotrexate (MTX). The cell population was expanded in roller bottles until sufficient numbers of cells were available for inoculating a bioreactor.

Prior to inoculation a S200 bioreactor underwent clean-in-place (CIP) and steam-in-place (SIP) cycles. It was then filled with CCM-3 medium containing 5% FBS and charged with 450 grams of microspheres. The microspheres were conditioned with medium prior to inoculation. The reactor was inoculated with cells and the operating parameters were: pH 7.2., 37° C., inlet (bottom of fluidized bed) dissolved $O_2$ between 100 and 400 torr, exit (top of fluidized bed) dissolved $O_2$ between 0 and 200 torr. Following an initial batch phase, medium perfusion was initiated, with periodic increases in rate so as to maintain the glucose concentration at 1.0 g/L. This was continued until a sufficient number of cells had accumulated in the reactor to inoculate a S2000 bioreactor. Following CIP and SIP, a S-2000 reactor was filled with CCM-3 medium supplemented with 5% FBS and 5 mM MTX and charged with 5000 grams of microspheres. These microspheres were conditioned with medium prior to inoculation. The operating conditions in respect of temperature, reactor arrangement and dissolved $O_2$ are as given above. The microspheres from the S-200 reactor were aseptically transferred into the S-2000 reactor to initiate batch phase. When the glucose concentration fell below 1.5 g/L, the growth phase was started by initiating medium perfusion (CCM-3, 5% FBS and 5 mM MTX) at a rate sufficient to maintain the glucose concentration at 1.0 g/L. Cell growth was monitored on-line by measuring oxygen uptake and glucose consumption rates. When a sufficient number of cells had accumulated within the reactor, the perfusion medium was changed to CCM-3 supplemented with 1% FBS and 5 mM MTX, transition medium. Again this perfusion rate was modified so as to maintain a glucose concentration of 1.0 g/L. Following further growth in the transition medium, the perfusion medium was changed once again to the production medium, CCM-3 supplemented with 5 mM MTX. The perfusion rate was increased to maintain a glucose concentration of 1.0 g/L. Thereafter, either exit dissolved $O_2$ or recycle flow rate setpoints were lowered to maintain control over the reactor. The production phase typically lasts for about 60 days.

Between 400 and 1600 liters of reactor permeate, stored a 4°–8° C., were processed through a Millipore Prostak Microfiltration Unit. The cell-free permeate from this operation supplied the ultrafiltration step. The permeate was concentrated 30–60× with a Millipore Spiral Wound System. Following concentration, the retentate was drained into a holding tank and the system was filled with 5–20 L of 50 mM phosphate buffer, pH 7.5. The wash buffer was drained from the system and combined with the retentate. The ultrafiltration concentrate was filtered through a prefilter and a terminal 0.22 mm filter into a previously autoclaved Nalgene bottle. Nominally 800 ml of concentrate are dispersed into each bottle and stored frozen.

As mentioned previously, the particular recombinant production system and the particular cell culturing protocol is outside the scope of this invention. The system and protocol discussed above are representative of the many options available to the skilled artisan and they are included herein for purposes of illustration only. For example media obtained from a stirred-tank bioreactor are equally suited as sources of conditioned media for use with the present invention. The purification protocol which is the subject of this invention is applicable, with only routine modification, to a variety of recombinant complement receptor and complement receptor-like proteins regardless of how they are produced or cultured.

The purified complement receptor proteins obtained by practicing the process of this invention have the following properties: 1) greater than 95% CR protein by weight; 2) stable to proteolytic degradation at 4° C. for at least three months; 3) low (<1 E.U./mg protein) endotoxin; 4) low (<1 pg/mg protein) DNA; 5) non-CR protein <5% by weight; and 6) virally inactive.

The following example further illustrates this invention but is not offered by way of limitation of the claims herein.

EXAMPLE I

INTRODUCTION

The procedure outlined below was developed for the isolation and purification of soluble complement receptor-1 (sCR1) from conditioned cell culture medium concentrate. This process is designed to prepare sCR1 of >95% protein purity while removing impurities derived from the host cell, cell culture medium, or other raw materials. The recovery procedure consists of nine steps including cation and anion exchange, immobilized metal affinity, hydrophobic interaction and size exclusion chromatography, and two viral inactivation treatments. Each step is described in detail below including materials, methods, and expected results. Steps 1 though 3 are carried out at 2°–8° C., and steps 6 through 9 are performed at 18°–25° C. All buffers are prepared with WFI and filtered through a 10,000 MWCO filter before use. All columns are monitored by UV absorbance at 280 nm and by conductivity, where indicated. Columns are cleaned and equilibrated before use, and cleaned and stored in NaOH after each use.

The process is scaled to accomodate approximately 1000 L of medium containing 100 G of crude sCR1, and requires 7–14 days to complete, depending on the scale of the operation.

STEP 1: MEDIA PRE-TREATMENT

While sting, the pH of 1000 L of cell-free conditioned medium is lowered to pH 5.2 by the addition of 1M acetic acid at a rate of 1–3 L/min. The volume of acetic acid required is approximately 3% the volume of the medium, and requires 15–30 minutes to add. The pH is monitored continuously therafter. The pH adjustment produces a heavy precipitate. Clarification is achieved by microfiltration through a series of two Millipore 30 inch Polygard-CR filters connected in tandem (0.5 micron). The sCR1 is recovered in the filtrate, and when 50–100 L of filtrate have accumulated, Step 2 is begun. This allows both the filtration and loading operations to occur simultaneously.

The acidification and filtration of the medium concentrate removes both non-sCR1 protein and non-proteinaceous material; and adjusts the sCR1 containing filtrate to the appropriate pH for subsequent S SEPHAROSE cation exchange chromatography.

STEP 2: PHARMACIA S SEPHAROSE FAST FLOW CHROMATOGRAPHY

The pH 5.2 filtrate is loaded at a flow rate of 150 cm/hr (and so throughout) onto a column of Pharmacia S Sepharose Fast Flow sulfonate substituted agaroses gel previously equilibrated with Buffer A. The column is washed at 150 cm/hr with 3–5 bed volumes of Buffer A, followed by 5–10 bed volumes of Buffer B. The sCR-1 is eluted with 3–5 bed volumes of Buffer C. The entire elution peak is collected until the absorbance decreases to 5% of the maximum observed absorbance. The sCR1 elutes in approximately 1.5–2 bed volumes.

The column is cleaned and recycled by treating for at least 1 hr with 0.5N NaOH, washing with WFI, and equilibrating with Buffer A. When not in use the column is stored in 0.01N NaOH.

The S SEPHAROSE cation exchange chromatography removes a large proportion of cell and media derived impurities (particularly protein) and concentrates sCR1 in the Buffer C column eluate for further processing.

STEP 3: IMAC USING TOYOPEARL AF-CHELATE 650M

PART 1: CHARGING IMAC COLUMN WITH COPPER AND EQUILIBRATION OF THE CHARGED COLUMN

The IDA-substituted polyvinyl methacrylate copolymer column is charged with copper as follows: 6–8 column volumes of 0.2% cupric sulfate is passed over the column after flushing with 3 column volumes of WFI. The column is charged until a blue color is evident over the whole bed, and excess copper is detected in the eluate stream. The column is then flushed with 1–2 bed volumes of WFI, followed by 3–5 bed volumes of Buffer C.

PART 2: LOAD, WASH, ELUTION, AND REGENERATION OF IMAC COLUMN

The S Sepharose cation exchange column eluate is loaded at a flow rate of 150 cm/hr (and so throughout) onto the IMAC column after charging and equilibration (see Step 3, Part 1). The column is washed at 150 cm/hr with 3–5 bed volumes of Buffer C, followed by 5–10 bed volumes of Buffer D. It is imperative that after flushing with Buffer D is complete, the column be flushed with 3–5 volumes of Buffer C to bring the pH back to 8, otherwise significant copper leaching will occur upon the application of Buffer E. The sCR1 is fluted with 3–5 bed volumes of Buffer E. The entire elution peak is collected until the absorbance decreases to 5% of the maximum observed absorbance. The sCR-1 elutes in approximately 2 bed volumes. The copper is removed by flushing with 5 bed volumes of 50 mM EDTA, since it is incompatible with the 0.5M NaOH sanitization. The concentrated copper effluent must be collected for proper disposal according to local codes.

The IMAC column is cleaned and recycled by treating for at least 1 hr with 0.5N NaOH, washing with WFI, and equilibrating with Buffer C. When not in use the column is stored in 0.01N NaOH.

The IMAC removes cell and media derived impurities (particularly protein and DNA).

STEP 4: VIRAL INACTIVATION WITH GUANIDINE AND ADDITION OF AMMONIUM SULFATE

PART 1: ADDITION OF GUANIDINE (PERFORMED AT 2°–8° C.)

The cold IMAC eluate is treated with guanidine by the addition of one-half volume of cold Buffer F with constant stirring, over a period of 10–15 minutes. When the addition of Buffer F is completed, the solution is transferred to a second vessel by subsurface transfer, and held for 6 minutes.

PART 2: ADDITION OF AMMONIUM SULFATE (PERFORMED AT 2°–8° C.)

The solution treated in Step 4, Part 1 is immediately diluted with an equal volume of cold Buffer G, over a 10–15 minute period, with constant stirring. The resulting solution is 1.0M in guanidine and 0.9M in ammonium sulfate, and should be at 2°–8° C. before performing Step 5.

The guanidine treating affords retroviral inactivation, and the addition of ammonium sulfate prepares the solution for hydrophobic interaction chromatography using a butyl-substituted ethylene glycol-methacrylate copolymer support, i.e., TOYOPEARL BUTYL chromatography.

STEP 5: TOYOPEARL BUTYL-650M CHROMATOGRAPHY (2°–8° C.)

The solution from Step 4 is loaded at a flow rate of 150 cm/hr onto a column of butyl substituted ethylene glycol-methacrylate copolymer support, i.e., TOYOPEARL Butyl-650M previously equilibrated with Buffer H. It is critical that the buffers and column are at 2°–8° C. When loading is completed the column is washed with 3–5 bed volumes of Buffer H, and the bound sCR1 is eluted with Buffer I. The sCR-1 elutes in 1.5–3 bed volumes. The column is stripped with 0.2N NaOH. The base wash elutes protein impurities in a measurable peak, which is neutralized and held for assay.

The HIC column is cleaned and recycled by treating for at least 1 hr with 0.5N NaOH, washing with WFI, and equilibrating with Buffer H. When not in use, the column is stored in 0.01N NaOH.

STEP 6: VIRAL INACTIVATION AT PH 11 AND DIAFILTRATION

The butyl eluate is adjusted to pH 11 by addition of 2.5M NaOH. The solution is immediately transferred to a second vessel by subsurface transfer, held at pH 11 for 16 minutes, and readjusted to pH 9.0 using 2.5M HCl. The pH 11 treated solution is then continuously diafiltered against Buffer J in a tangential flow apparatus equipped with 30 kD MWCO low-protein binding membranes (such as Filtron Omega series). The diafiltration continues until 4–5 volumes have passed into the permeate, and the conductivity of the retentate is $\leq 2$ mS/cm.

The pH 11 treating affords retroviral inactivation, and the diafiltration prepares the sCR1 solution for DEAE-derivitized ethylene glycol-methacrylate copolymer anion exchange chromatography.

STEP 7: TOYOPEARL DEAE-650S ANION EXCHANGE CHROMATOGRAPHY

The solution from Step 6 is loaded at a flow rate of 150 cm/hr onto a column of DEAE-derivitized ethylene glycol-methacrylate copolymer, i.e., TOYOPEARL, DEAE-650S, previously equilibrated with Buffer J. After loading, the column is washed with 3–5 bed volumes of Buffer J. The bound sCR1 is eluted with a 5-column volume linear gradient starting from 100% Buffer J and extending to 100% Buffer K. The entire elution peak is collected until the absorbance decreases to 20% of the maximum absorbance. Collection is then switched to a second container for the tailing end of the peak. The sCR-1 should elute in 1–2 bed volumes. The column is stripped by washing with 3 bed volumes of Buffer L.

The DEAE anion exchange column is cleaned and recycled by treating for at least 1 hr with 0.5N NaOH, washing with WFI, and equilibrating with Buffer J. When not in use the column is stored in 0.01N NaOH.

The DEAE anion exchange chromatography removes protein, DNA, and potential viral impurities.

STEP 8: TOYOPEARL HW-55F CHROMATOGRAPHY

The DEAE anion exchange column eluate is loaded at a flow rate of 20 cm/hr onto a size exclusion gel column of TOYOPEARL HW-55F previously equilibrated with Buffer M. The volume of the load should be $\leq 10\%$ of the total bed volume, and the concentration of the load should be $\leq 5$ mg/ml. Collect the entire peak until the absorbance decreases to 10% of the maximum absorbance. Collection is then switched to a second container for the tail of the peak. If multiple injections are required, pool the peak fractions. The material is now ready for final concentration.

The size exclusion column is cleaned and recycled by treating for at least 1 hr with 0.5N NaOH, washing with WFI, and equilibrating with Buffer M. When not in use the column is stored in 0.01N NaOH.

The size exclusion chromatography removes the last traces of low molecular weight protein impurities, and serves to exchange the sCR1 into a solution containing components compatible with the final formulation buffer, Buffer N.

STEP 9: CONCENTRATION AND FINAL FILTRATION

The TOYOPEARL HW-55F size exclusion column eluate is concentrated to 5–6 mg/mL using a tangential flow ultrafiltration device appropriately sized to the final volume expected (such as a Pharmacia Minisette Ultrafiltration unit or Millipore CUF unit) fitted with Filtron Omega series 30 kD or 100 kD MWCO membranes. Following concentration, the solution is then continuously diafiltered against 5 volumes of Buffer N. The concentrated sCR-1 is filtered through a Millipore 0.2 micron Millipak filter into sterile containers.

BUFFERS

| Buffer A | 20 mM sodium phosphate, 60 mM NaCl, pH 5.2 |
| Buffer B | 20 mM sodium phosphate, 100 mM NaCl, pH 6.0 |
| Buffer C | 100 mM sodium phosphate, 500 mM NaCl, pH 8.0 |
| Buffer D | 100 mM acetate, 1 M NaCl, pH 4.0 |
| Buffer E | 50 mM imidazole, 100 mM sodium phosphate, 500 mM NaCl, pH 8.0 |
| Buffer F | 6 M guanidine hydrochloride, 100 mM sodium phosphate, pH 7.0 |
| Buffer G | 1.8 M ammonium sulfate, 100 mM sodium phosphate, pH 7.0 |
| Buffer H | 0.9 M ammonium sulfate, 100 mM sodium phosphate, pH 7.0 |
| Buffer I | 100 mM sodium phosphate, pH 7.0 |
| Buffer J | 50 mM Tris/Tris, HCl, pH 9.0 |
| Buffer K | 50 mM Tris/Tris, HCl, 0.2 M NaCl, pH 9.0 |
| Buffer L | 50 mM Tris/Tris, HCl, 1.0 M NaCl, pH 9.0 |
| Buffer M | 10 mM sodium phosphate, 0.9% w/v NaCl, pH 7.0 |
| Buffer N | 16.3 mM potassium phosphate, 25 mM NaCl, 2% (w/v) mannitol, pH 6.9 |

SOLUTIONS

WFI 2.5 M sodium hydroxide
0.5 M sodium hydroxide
0.2 M sodium hydroxide
0.01 M sodium hydroxide
2.5 M hydrochloric acid
1 M acetic acid
0.2% (w/v) cupric sulfate, pentahydrate ($CuSO_4 \cdot 5H_2O$)
50 mM edetate di- or tetrasodium ($Na_2EDTA$ or $N_4EDTA$)

COLUMN PARAMETERS

| Column | Minimum Length, cm | Maximum Flow Rate, cm/hr | Load Ratio | Units for Load Ratio |
|---|---|---|---|---|
| S Sepharose | 10 | 150 | 10 | . . . grams sCR-1 per liter bed volume |
| IMAC | 10 | 150 | 8 | . . . grams protein per liter bed volume |
| BUTYL | 10 | 150 | 9 | . . . grams protein per liter bed volume |
| DEAE | 10 | 150 | 10 | . . . grams protein per liter bed volume |
| HW-55F | 45 | 30 | <10% . . . & <5 mg/mL . . . | . . . of column volume protein |

PURIFICATION TABLE

| Step | Volume (L) | [sCR.1] G/L) | [Protein] (G/L) | Total sCR-1 (G) | . . . Protein (G) | Cumulative Recovery (%) |
|---|---|---|---|---|---|---|
| Medium | 905 | 0.05 | n. d. | 46.2 | n. d. | 100 |
| SSFF Eluate | 45.7 | 0.95 | 2.49 | 43.3 | 11.8 | 94 |
| IMAC Eluate | 43.4 | 1.00 | 1.82 | 44.1 | 81.9 | 96 |
| Butyl Eluate | 21.6 | 2.10 | 2.24 | 45.2 | 50.1 | 98 |
| DEAE Eluate | 10.0 | 4.08 | 3.94 | 40.8 | 39.4 | 89 |
| HW-55F Eluate | 21.7 | 1.68 | 1.65 | 36.4 | 35.8 | 79 |
| Purified sCR-1 | 6.8 | 5.33 | 5.18 | 36.3 | 35.3 | 79 | sCR-1 assayed by HPLC
Protein assayed by absorbance at 280 nm ($\epsilon = 1.10$ mL mg$^{-1}$ cm$^{-1}$)

What is claimed is:

1. A method for purifying a complement receptor protein from a mixture containing same comprising sequentially contacting said mixture with a cationic chromatographic support, metal affinity chromatographic support, a size exclusion chromatographic support and selectively eluting the protein from each support.

2. The method according to claim 1 wherein the receptor is selected from the group consisting of CR1, CR2, CR3 and CR4.

3. The method according to claim 2 wherein the receptor is CR1 and fragments thereof.

4. The method according to claim 3 wherein the receptor is a soluble fragment of CR1.

5. The method according to claim 4 wherein the receptor is TP10HD.

6. The method according to claim 1 wherein the cationic chromatographic support is selected from the group consisting of carboxymethyl-substituted cellulose, crosslinked carboxymethyl- and sulfopropyl-substituted dextrans, carboxymethyl- and sulfonate-substituted agarose, and carboxymethyl-derivitized ethylene glycol-methacrylate copolymers, and elution is by addition of a buffered salt solution.

7. The method according to claim 6 wherein the support is sulfonate-substituted agarose beads and the salt is NaCl.

8. The method according to claim 6 wherein the salt solution is 100 mM sodium phosphate, 500 mM NaCl, pH 8.0.

9. The method according to claim 1 wherein the metal affinity support is selected from the group consisting of silica, agarose and polyvinyl-methacrylate copolymers.

10. The method according to claim 9 wherein the support is substituted and the substituent is selected from the group consisting of iminodiacetic acid (IDA) and tris (carboxymethyl)ethylene diamine (TED).

11. The method according to claim 10 wherein the support is a polyvinyl-methacrylate copolymer substituted with IDA.

12. The method according to claim 1 wherein the metal affinity support is a polyvinyl-methacrylate copolymer substituted with IDA and the complement receptor protein is selectively eluted with an imidazole salt buffer.

13. The method according to claim 12 wherein imidazole salt elution buffer comprises 50 mM imidazole, 100 mM sodium phosphate, 500 mM NaCl, pH 8.0.

14. The method according to claim 1 wherein the size exclusion chromatographic support is selected from the group consisting of crosslinked dextrans, polyacrylamides, agarose beads, and ethylene glycol-methacrylate copolymer matrices.

15. The method according to claim 14, wherein the support is an ethylene glycol-methacrylate copolymer and the elution is with 10 mM sodium phosphate, 0.9% w/v NaCl, pH 7.0.

16. A method for the purification of a complement receptor protein from conditioned cell culture medium containing same comprising sequentially subjecting the medium to (a) cationic exchange chromatography, (b) immobilized metal affinity chromatography, (c) hydrophobic interaction chromatography, (d) anionic exchange chromatography, and (e) size exclusion chromatography.

17. The method according to claim 16 wherein the cationic exchange chromatography step employs a support selected from the group consisting of carboxymethyl-cellulose, crosslinked carboxymethyl- and sulfopropyl-dextrans, carboxymethyl- and sulfonate-agarose beads, and carboxymethyl-derivitized ethylene glycol-methacrylate copolymer, and elution is by a buffered salt solution.

18. The method according to claim 17 wherein the support is sulfonate-substituted agarose beads and the salt is NaCl.

19. The method according to claim 18 wherein the salt solution is 100 mM sodium phosphate, 500 mM NaCl, pH 8.0.

20. The method according to claim 17 wherein the immobilized metal affinity chromatography support is selected from the group consisting of silica, agarose, and polyvinyl-methacrylate copolymers.

21. The method according to claim 20 wherein the support is substituted and the substituent is selected from the group consisting of iminodiacetic acid (IDA) and tris (carboxymethyl)ethylene diamine (TED).

22. The method according to claim 21 wherein the support is a polyvinyl-methacrylate copolymer substituted with IDA.

23. The method according to claim 16 wherein the immobilized metal affinity chromatography support is a polyvinyl-methacrylate copolymer substituted with IDA and the complement receptor protein is selectively eluted with an imidazole salt buffer.

24. The method according to claim 23 wherein imidazole salt elution buffer comprises 50 mM imidazole, 100 mM sodium phosphate, 500 mM NaCl, pH 8.0.

25. The method according to claim 16 wherein the hydrophobic interaction chromatographic support is selected from the group consisting of $C_2$–$C_{10}$ alkyl-substituted agarose, aryl-substituted agarose, alkyl-substituted silica, and alkyl-substituted organic polymer resin.

26. The method according to claim 25 wherein the support is selected from the group consisting of butyl-, phenyl- and octyl-substituted agarose beads and butyl-, phenyl- and ether-substituted ethylene glycol-methacrylate copolymers.

27. The method according to claim 26 wherein the support is a butyl-substituted ethylene glycol-methacrylate copolymer.

28. The method according to claim 20 wherein the support is a butyl-substituted ethylene glycol-methacrylate copolymer and the protein is selectively eluted with a low salt buffer.

29. The method according to claim 28 wherein the protein is selectively eluted with a buffer containing 100 mM sodium phosphate, pH 7.0.

30. The method according to claim 16 wherein said anionic exchange chromatography employs a support selected from the group consisting of diethylaminoethyl-substituted cellulose, crosslinked diethylaminoethyl-substituted dextan, quarternary aminoethyl-substituted dextrans, diethylaminoethyl-substituted agarose, quarternary amino-substituted agarose, and diethylaminoethyl-derivitized ethylene glycol-methacrylate copolymer.

31. The method according to claim 30 wherein said support is diethylaminoethyl-derivitized ethylene glycol-methacrylate copolymer.

32. The method according to claim 16 wherein the size exclusion chromatography step employs a support selected from the group consisting of crosslinked dextrans, polyacrylamides, agarose beads, and ethylene glycol-methacrylate copolymer matrices.

33. The method according to claim 32 wherein the support is an ethylene glycol-methacrylate copolymer.

34. A method for purifying a complement receptor protein from a conditioned cell medium comprising:
   (a) concentrating the conditioned cell medium;
   (b) adsorbing the complement receptor protein onto a cationic chromatographic support;
   (c) washing the adsorbed protein with at least one buffer;
   (d) eluting the washed protein onto an immobilized metal affinity chromatographic support;

(e) adsorbing the eluted protein from step (d);

(f) washing the adsorbed protein with at least one buffer;

(g) eluting the washed protein;

(h) adsorbing the eluted protein from step (g) onto a hydrophobic interaction chromatographic support;

(i) selectively eluting the protein;

(j) adsorbing the eluate from step (i) onto an anionic exchange support;

(k) eluting the adsorbed protein;

(l) subjecting the eluate from step (k) to size exclusion chromatography and (m) recovering the protein therefrom.

35. The method according to claim 34 which includes the optional step or steps of inactivating viruses, if present.

36. The method according to claim 35 wherein said viral inactivation step or steps is performed after step (i) and before step (j) and/or is performed after step (g) and before step (h).

37. The method according to claim 36 wherein said viral inactivation step(s) comprises treatment of the eluate with base or with guanidine hydrochloride.

38. The method according to claim 34 wherein the cationic exchange chromatographic support of step (b) is sulfonate-substituted agarose beads.

39. The method according to claim 34 wherein the immobilized metal affinity chromatographic support is a polyvinyl-methacrylate copolymer substituted with IDA.

40. The method according to claim 34 wherein the anionic exchange chromatographic support of step (j) is selected from the group consisting of diethylaminoethyl, quaternary animoethyl and quaternary amine substituted resins, which resins are selected from the group consisting of crosslinked dextrans, agarose, and ethylene glycol-methacrylate copolymers.

41. The method according to claim 40 wherein the anionic exchange chromatographic support is a diethylaminoethyl-substituted ethylene glycol-methacrylate copolymer.

42. The method according to claim 34 wherein the hydrophobic interaction chromatographic support of step (h) is selected from the group consisting of $C_2$–$C_{10}$ alkyl-substituted agarose, aryl-substituted agarose, alkyl-substituted silica, and alkyl-substituted organic polymer resin.

43. The method according to claim 42 wherein the support is selected from the group consisting of butyl-, phenyl- and octyl-substituted agarose beads and butyl-, phenyl- and ether-substituted ethylene glycol-methacrylate copolymers.

44. The method according to claim 43 wherein the support is a butyl-substituted ethylene glycol-methacrylate copolymer.

45. The method according to any of claim 35 wherein the size exclusion chromatography step employs an ethylene glycol-methacrylate copolymer gel.

46. The method of claim 34 wherein said protein is recovered by pooling and concentrating the protein containing fractions from chromatography step (l) by ultrafiltration.

* * * * *